(12) United States Patent
Kamishita

(10) Patent No.: US 8,136,703 B2
(45) Date of Patent: Mar. 20, 2012

(54) FLUID CONTAINER AND AIRLESS FLUID DISPENSING SYSTEM

(75) Inventor: Taizou Kamishita, Osaka (JP)

(73) Assignees: Toko Yakuhin Kogyo Kabushiki Kaisha, Osaka (JP); Shinko Chemical Co., Ltd., Ishikawa (JP)

( * ) Notice: Subject to any disclaimer, the term of this patent is extended or adjusted under 35 U.S.C. 154(b) by 827 days.

(21) Appl. No.: 12/226,298

(22) PCT Filed: Apr. 20, 2007

(86) PCT No.: PCT/JP2007/058640
§ 371 (c)(1),
(2), (4) Date: Oct. 14, 2008

(87) PCT Pub. No.: WO2007/123207
PCT Pub. Date: Nov. 1, 2007

(65) Prior Publication Data
US 2009/0289083 A1     Nov. 26, 2009

(30) Foreign Application Priority Data
Apr. 21, 2006  (JP) .................................. 2006-118192

(51) Int. Cl.
*G01F 11/00*  (2006.01)
(52) U.S. Cl. ...................... 222/256; 222/386; 222/321.6
(58) Field of Classification Search .................. 222/256, 222/321.1, 321.6–321.9, 386, 389, 394, 383.1, 222/383.3
See application file for complete search history.

(56) References Cited

U.S. PATENT DOCUMENTS 5,000,355 A * 3/1991 Pritchard ...................... 222/256
5,052,592 A    10/1991 Wilken et al.
(Continued)

FOREIGN PATENT DOCUMENTS

JP         59-55920         4/1984
(Continued)

OTHER PUBLICATIONS

Datta et al. "Development of a new nasal drug delivery system of diazepam with natural mucoadhesive agent from *Trigonella foenum-graecum* L". *Journal of Scientific and Industrial Research*, vol. 64, pp. 973-977 (2005).

(Continued)

*Primary Examiner* — Kevin P Shaver
*Assistant Examiner* — Donnell Long
(74) *Attorney, Agent, or Firm* — Hamre, Schumann, Mueller & Larson, P.C.

(57) ABSTRACT

A fluid container according to the present invention includes a container body having upper and lower openings, and further having a shoulder member and a side wall which extend between the upper and lower openings. The fluid container also includes a spacer abutting on the shoulder member of the container body, and a slidable valve slidably moving along an inner surface of the side wall of the container body in a hermetically sealed manner. The slidable valve defines a container space for holding fluid, in conjunction with the side wall of the container body. Further, a bottom cover is provided for covering across the lower opening of the container body. The spacer and the slidable valve include a spacer surface and a valve surface, respectively, which oppose to each other and are inclined at tilt angles between 5 and 30 degrees relative to a horizontal surface. Therefore, an airless fluid dispensing system using the fluid container securely prevents a small air bubble from being trapped in the container body when filled in with the fluid, thereby to dispense a constant dosage without requiring undesired pumping actions prior to actual use.

13 Claims, 15 Drawing Sheets

U.S. PATENT DOCUMENTS

| | | | |
|---|---|---|---|
| 5,125,539 A * | 6/1992 | Schneider | 222/144.5 |
| 5,158,761 A | 10/1992 | Kamishta et al. | |
| 5,215,739 A | 6/1993 | Kamishita et al. | |
| 5,782,345 A | 7/1998 | Guasch et al. | |
| 5,862,955 A * | 1/1999 | Albini et al. | 222/212 |
| 6,596,704 B1 | 7/2003 | Court et al. | |
| 7,306,123 B2 * | 12/2007 | Masuda | 222/386 |
| 2003/0073676 A1 | 4/2003 | Biggadike et al. | |
| 2003/0230600 A1 * | 12/2003 | Masuda | 222/321.7 |

FOREIGN PATENT DOCUMENTS

| | | | |
|---|---|---|---|
| JP | 2-264714 | | 10/1990 |
| JP | 6-23094 | | 3/1994 |
| JP | 2003-212262 | | 7/2003 |
| JP | 2003212262 | * | 7/2003 |
| JP | 2004-99591 | | 4/2004 |
| JP | 2004-189731 | | 7/2004 |
| JP | 2006-44710 | | 2/2006 |
| JP | 2006044710 | * | 2/2006 |
| JP | 2006-83081 | | 3/2006 |
| JP | 2008-44649 | | 2/2008 |
| RU | 2 157 682 | | 10/2000 |
| WO | WO 99/34776 | | 7/1999 |

OTHER PUBLICATIONS

Co-pending U.S. Appl. No. 12/226,287 entitled Sprayable Gel-Type Skin/Mucosa-Adhesive Preparation and Administration System Using the Preparation filed Oct. 14, 2008.

* cited by examiner

Fig.1A
Fig.1B
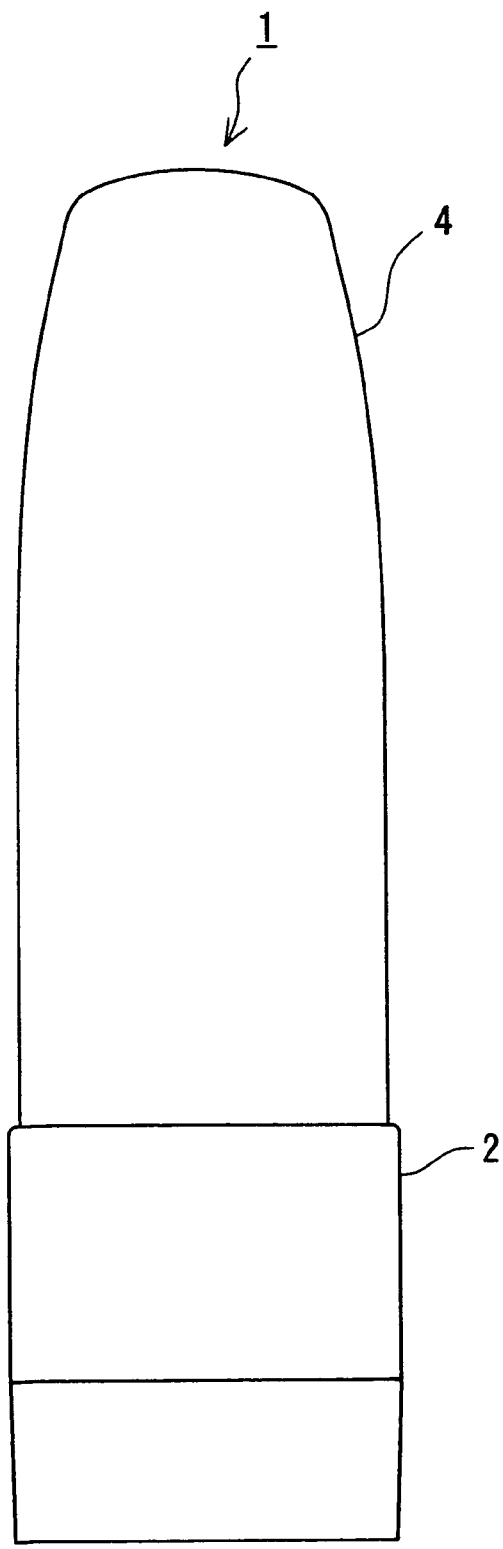
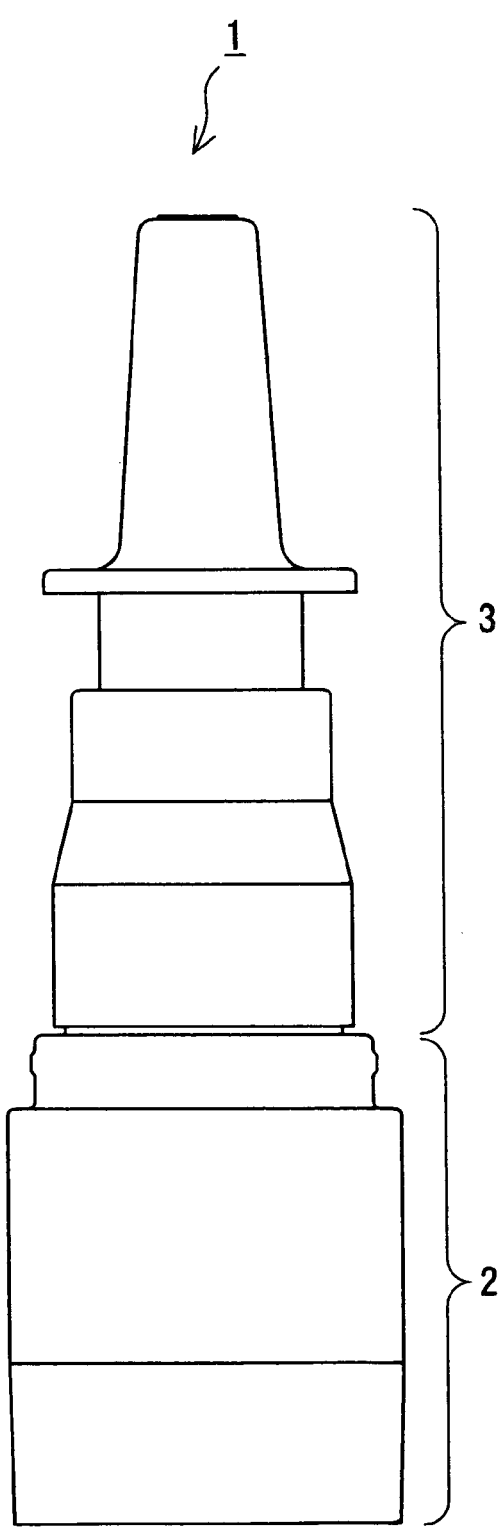

Fig.5A
Fig.5B
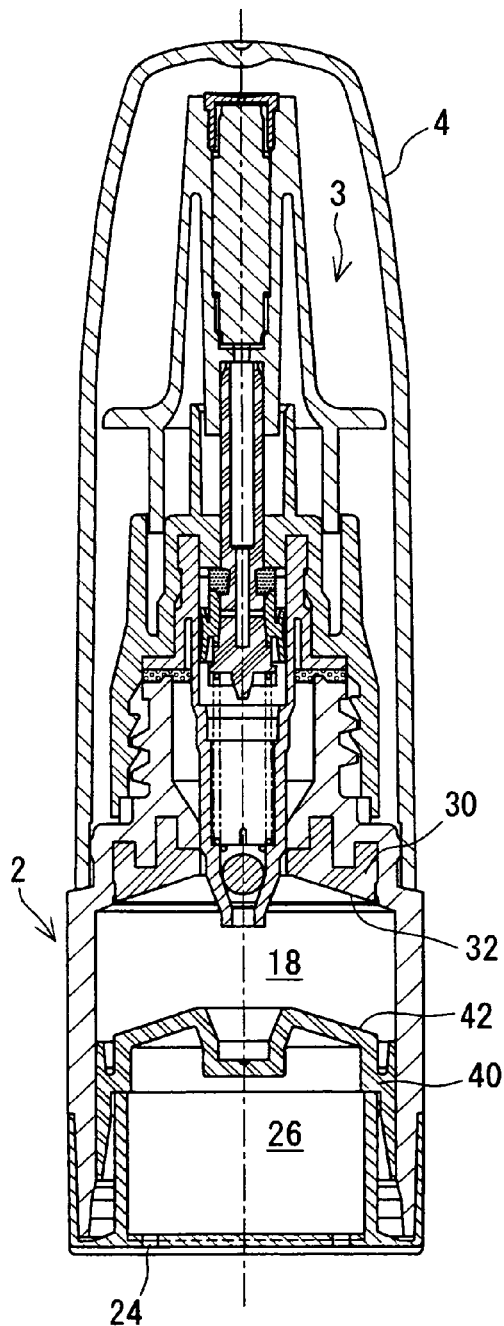
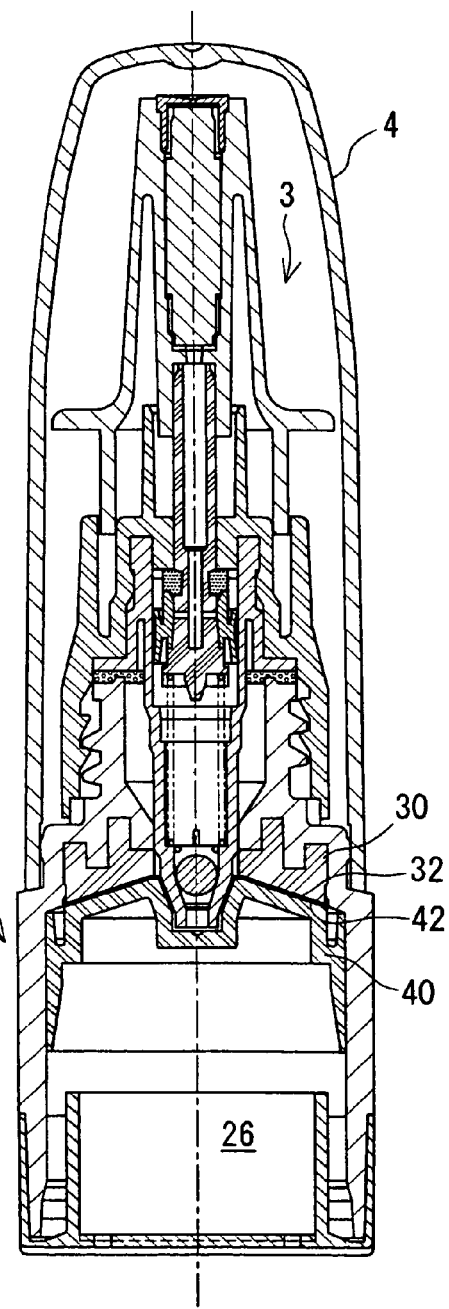

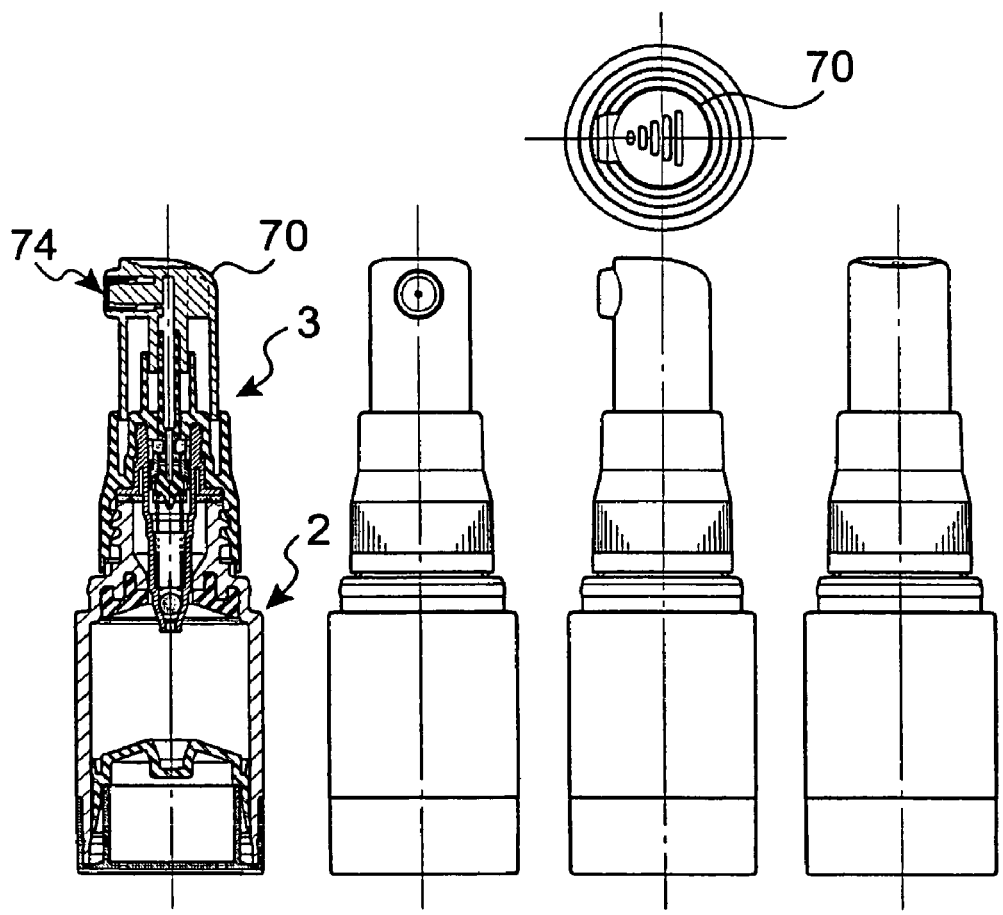

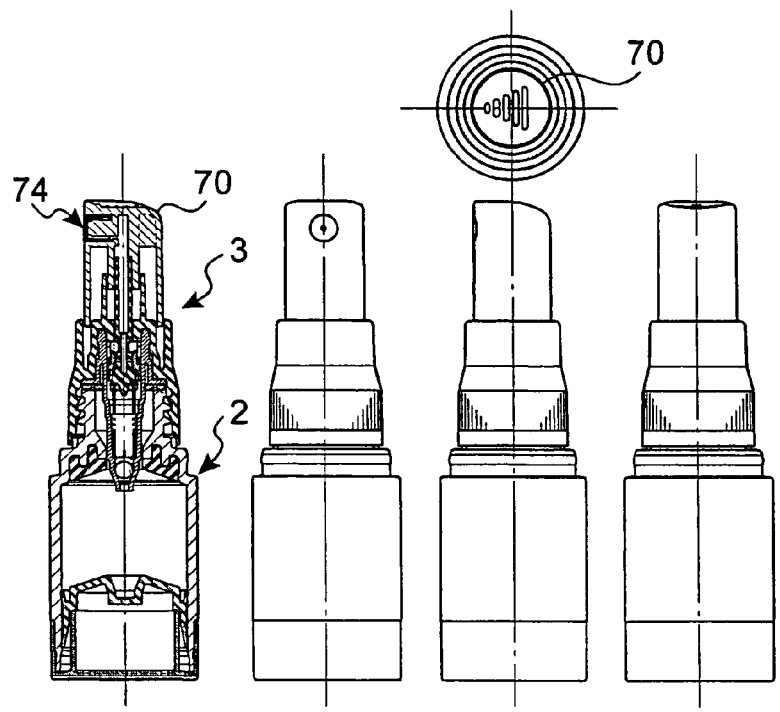
Fig.11E
Fig.11A  Fig.11B  Fig.11C  Fig.11D
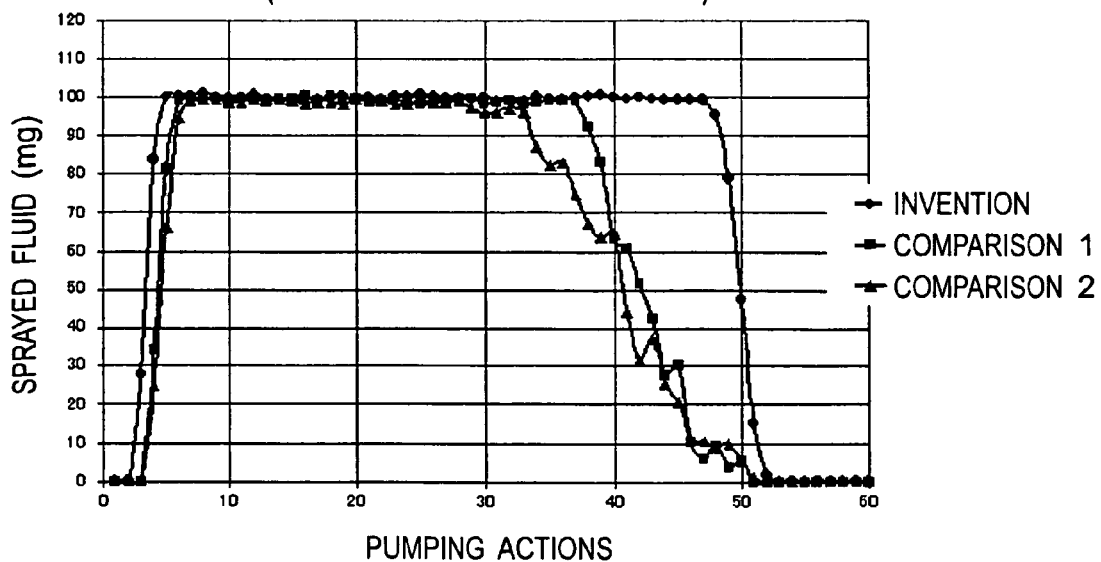
Fig.12

FLUID CONTAINER AND AIRLESS FLUID DISPENSING SYSTEM

TECHNICAL FIELD

The present invention relates to a fluid container and an airless fluid dispensing system using thereof.

BACKGROUND ART

An airless fluid dispensing system has been used in various applications for dispensing or applying fluids to an application site, which contains agents including medical products such as a nasal formulation, quasi-medical products such as a hair growth tonic, and cosmetic products such as a perfume.

Several airless fluid dispensing systems have so far been proposed, for example, Patent Document 1 discloses an airless pump container which includes a container body for holding fluid and an airless pump. The airless pump is adapted to pressurize fluid within a suction chamber upon downward depression of a nozzle, and release it into the atmosphere to spray the fluid from the nozzle, and also adapted to suck the fluid from the container body into the suction chamber upon upward return of the nozzle (see FIG. 2 thereof). The container body is provided with a bottom flap which is designed to slidably move along the side wall thereof upon receiving the atmospheric pressure, and in particular, moves upwardly with negative pressure in the container body as the fluid is sucked from the container body into the suction chamber. Thus, according to the airless pump container of Patent Document 1, even after the fluid within the container chamber is dispensed or sprayed, air is prevented from being introduced into the container body. Also, the invention of Patent Document 1 addresses to improve air-tightness (hermetic feature) between the bottom flap and the inner wall of the container body without increasing a sliding friction, by providing lower and upper inclined arms of resilient material with the bottom flap at the peripheral thereof contacting with the inner wall of the container body (see FIG. 3(A) thereof).

Another Patent Document 2 discloses a pump-type container with a content discharging mechanism which has a structure similar to that of Patent Document 1. The pump-type container has drawbacks, i.e., that some unused fluid is remained in an annular space between the container body and the bottom flap even after completion of the user's usage, and that an air bubble is trapped also in the annular space between the container body and the bottom flap when filled in with the fluid by a manufacturer. If the air bubble is trapped in the container body or the annular space, the user has to perform some pumping actions that is not required for actual dispense of the fluid to evacuate the air bubble from the container body and the suction chamber. Otherwise, a dosage of fluid may contain various volume, which is disadvantage especially when required to dispense a constant volume of the fluid such as medical products. However, repeating several pumping actions typically wastes the fluid for actual dosages. Therefore, the invention of Patent Document 2 suggests a substitution ceiling member having a flat bottom surface provided in the annular space of the container body, to eliminate unused fluid remained in an annular space between the container body and the bottom flap after completion of the usage, and the air bubble trapped when filled in with the fluid (see FIG. 1 thereof).

Patent Document 1: JPA 2003-212262
Patent Document 2: JPA 2006-044710

DISCLOSURE OF INVENTION

Problems to be Solved by Invention

Although provision of the substitution ceiling member according to Patent Document 2 may reduce the air bubble trapped in the container body to some extent, still, the air bubble is inevitably attached on the flat bottom surface of the substitution ceiling member, which requires the undesired pumping actions to evacuate the trapped air bubble. Thus, the substitution ceiling member according to Patent Document 2 is insufficient means for preventing the air bubble trapped in the container body when filled with the fluid. Therefore, another container body has been desired which can evacuate the air bubble in an easy and secure manner even if the air bubble is tapped within the container body. Also, it should be noted that Patent Document 1 merely describes the improvement of the slidable bottom flap but nothing about evacuation of the trapped air bubble.

Means to Solve the Problems

Therefore, one of aspects of the present invention is to provide a fluid container and an airless fluid dispensing system using thereof, which can prevent the small air bubble from being attached in the container body when filled in with the fluid.

The fluid container according to one of aspects of the present invention includes a container body having upper and lower openings, and further having a shoulder member and a side wall which extend between the upper and lower openings. The fluid container also includes a spacer abutting on the shoulder member of the container body, and a slidable valve slidably moving along an inner surface of the side wall of the container body in a hermetically sealed manner. The slidable valve defines a container space for holding fluid, in conjunction with the side wall of the container body. Further, a bottom cover is provided for covering across the lower opening of the container body. The spacer and the slidable valve include a spacer surface and a valve surface, respectively, which oppose to each other and are inclined at tilt angles between 5 and 30 degrees relative to a horizontal surface.

Preferably, the spacer surface and the valve surface have configurations complementary to each other. Also, the spacer may be integrally formed with the side wall of the container body. Further, the spacer surface is formed to be substantially continuous with the inner surface of the side wall via a curved surface.

The spacer may be made of low-density polyethylene, and at least one the spacer and slidable valve may be made of elastic material. Also, the tilt angle of the spacer surface relative to the horizontal surface may be set greater than the tilt angle of the valve surface relative to the horizontal surface.

The bottom cover may include a groove extending along a bottom surface thereof, the bottom cover having a through-hole through which a pressurizing space hermetically sealed by the side wall of the container body, the slidable valve, and the bottom cover may be in communication with the ambient air.

An airless pump may hermetically be connected to the upper opening of the fluid container.

Advantages of Invention

According to one of aspects of the airless fluid dispensing system of the present invention, a small air bubble is securely prevented from being trapped in the container body when filled in with the fluid, thereby to dispense a constant dosage without requiring undesired pumping actions prior to actual use.

BRIEF DESCRIPTION OF DRAWINGS

FIG. 1A is an elevational view of the airless fluid dispensing system according to the first embodiment of the present invention, and FIG. 1B is an elevational view similar to FIG. 1A with a cap removed.

FIGS. 5A and 5B are cross sectional views of the airless fluid dispensing system of FIG. 1, showing the conditions before and after dispensing the fluid, respectively.

FIGS. 10A-10E are cross sectional view, front elevational view, side view, back elevational view, and top plan view, respectively, of the airless fluid dispensing system of Modification 2.

FIGS. 11A-11E are cross sectional view, front elevational view, side view, back elevational view, and top plan view, respectively, of another airless fluid dispensing system of Modification 2.

FIG. 12 is a chart showing relationship between fluid weight (viscosity: 1000 mPa·s) sprayed by each pumping action and the number of pumping actions.

BRIEF DESCRIPTION OF REFERENCE NUMERALS

1: airless fluid dispensing system, 2: fluid container, 3: airless pump, 4: cap, 5: external thread, 6: internal thread, 10: container body, 11: upper opening, 12: lower opening, 13, 13': shoulder member, 14: side wall, 15: inner surface, 16: outer surface, 18: container space, 19: curved surface, 20: bottom cover, 22: groove, 24: through-hole, 26: pressurizing space, 30: annular spacer, 32: spacer surface, 32': shoulder surface, 40: slidable valve, 42: valve surface, 50: pump housing, 70: spout, 51: cylinder, 52: cylinder flange, 53: gasket, 54: piston, 55: vertical bore, 56: horizontal bore, 57: annular stopper, 58: annular sealing valve, 59: bottom reduced-diameter portion, 60: suction inlet, 61: ball valve, 62: coil spring, 63: suction chamber, 64: annular slit, 65: upper end, 70: spout, 71: inner wall, 72: solid rod, 73: through-channel, 74: spraying outlet, 75: nozzle, 76: annular flange, 77: tubular guiding wall, 78: lower end.

BEST MODE FOR CARRYING OUT THE INVENTION

With reference to attached drawings, embodiments of a fluid container and an airless fluid dispensing system using thereof according to the present invention will be described hereinafter. In the following description, directional terms such as "upper", "lower", "horizontal" and "vertical" are conveniently used for better understandings, yet, those terms are not intended as limiting the scope of the present invention. Also, like components are denoted by like reference signs throughout the attached drawings.

First Embodiment

Referring to FIGS. 1-7, a first embodiment of the airless fluid dispensing system according to the present invention will be described herein. FIG. 1A is an elevational view of the airless fluid dispensing system 1 of the first embodiment, and FIG. 1B is an elevational view similar to FIG. 1A, with a cap removed. The airless fluid dispensing system 1 of the first embodiment includes, in general, a fluid container 2, an airless pump 3, and the cap 4 encapsulating the fluid container 2. As described above, FIG. 1A shows the system 1 with the cap 4 while being unused, and FIG. 1B shows the system 1 without the cap 4, which is ready for use. The cap 4 has an inside surface with a notch (not shown), and the fluid container 2 has an outer surface with a boss which is snap fit within the notch so that the cap 4 is detachably attached with the fluid container 2.

Figure 2:
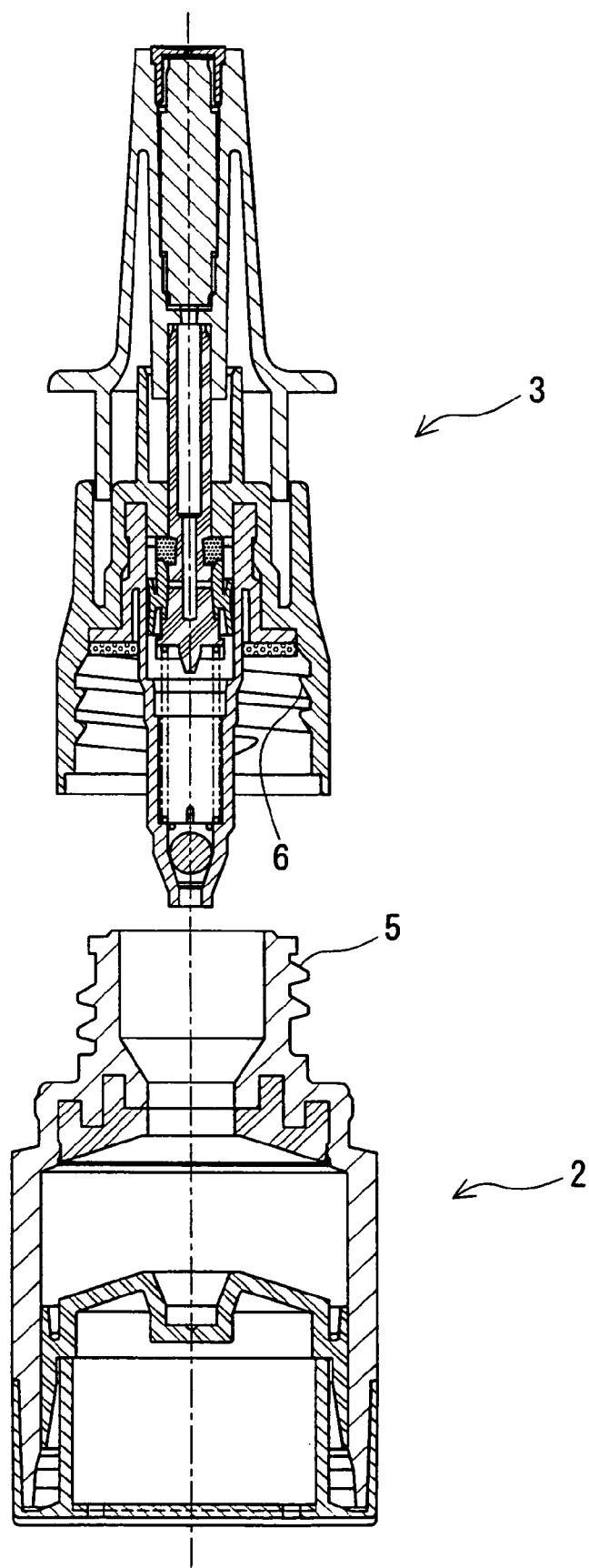
FIG. 2 is an exploded cross sectional view of the airless fluid dispensing system of FIG. 1, with the fluid container dismounted from the airless pump.

FIG. 2 is an exploded cross sectional view of the airless fluid dispensing system 1, with the fluid container 2 dismounted from the airless pump 3. Sealing connection between the fluid container 2 and the airless pump 3 can be achieved by engagement of an external thread 5 of the fluid container 2 with an internal thread 6 of the airless pump 3.

Figure 3:
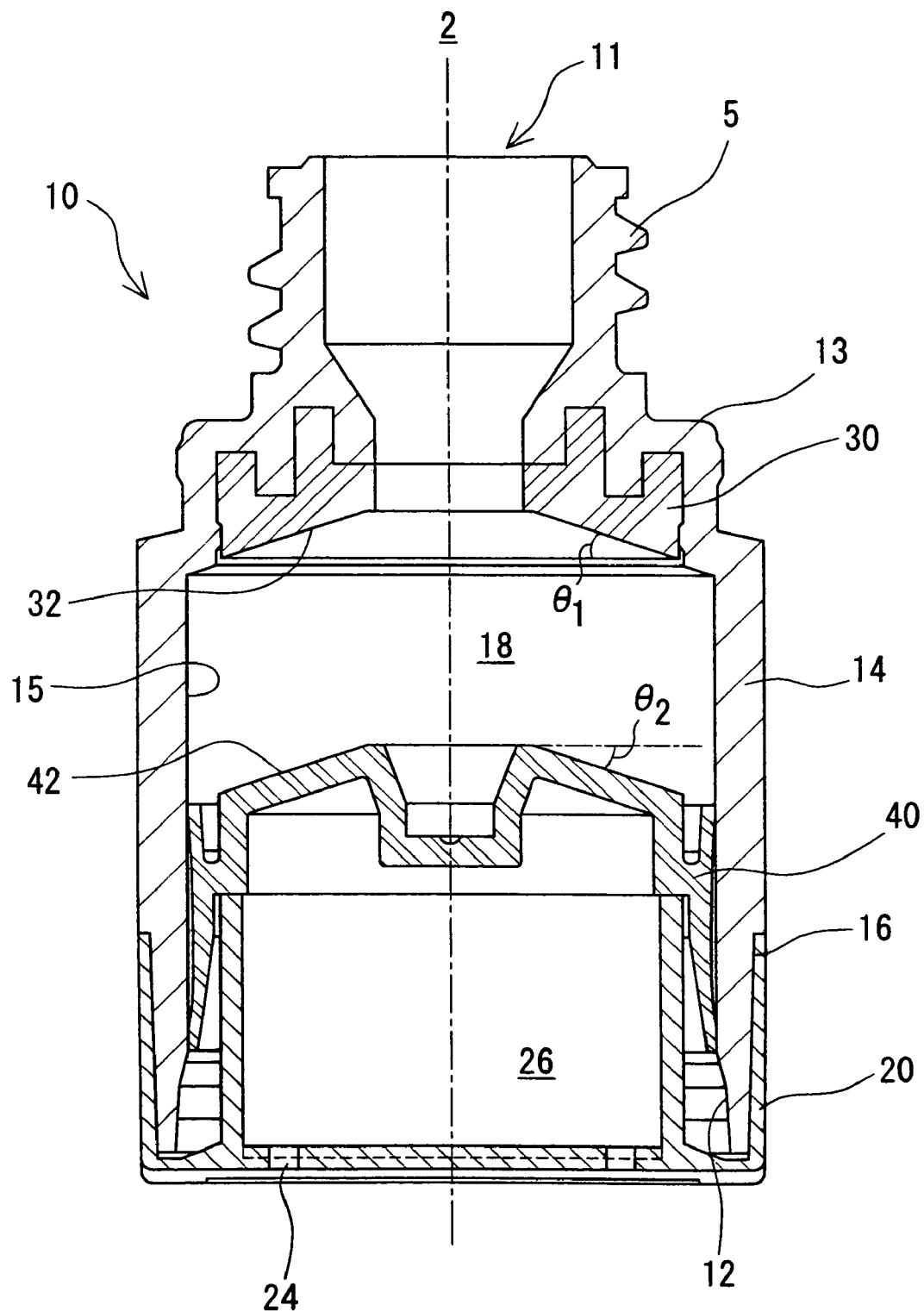
FIG. 3 is an enlarged cross sectional view of the fluid container of FIG. 2.

The fluid container 2 is further described herein with reference to FIG. 3 which shows an enlarged cross sectional view thereof. The fluid container 2 generally includes a hollow container body 10 having upper and lower openings 11, 12, a bottom cover 20 covering across the lower opening 12 of the container body 10. The container body 10 has a shoulder member 13 and a side wall 14, and the bottom cover 20 is adapted to engage with an outer surface of the side wall 14. The container body 10 and the bottom cover 20 of the present embodiment is shaped in a substantially circular when viewed from the top, any other shapes such as a polygonal shape can be adapted.

The fluid container 2 further includes an annular spacer 30 which is inserted from the lower opening 12 up to abut on the shoulder member 13 within the container body 10, and a slidable valve 40 which is inserted from the lower opening 12 and slidably moves along an inner surface 15 of the side wall 14 in a hermetically sealed manner. Thus, as illustrated in FIG. 3, a container space 18 for holding the fluid is defined between a spacer surface 32 of the annular spacer 30, a valve surface 42 of the slidable valve 40 opposing thereto, and the inner surface 15 of the side wall 14.

Figure 4:
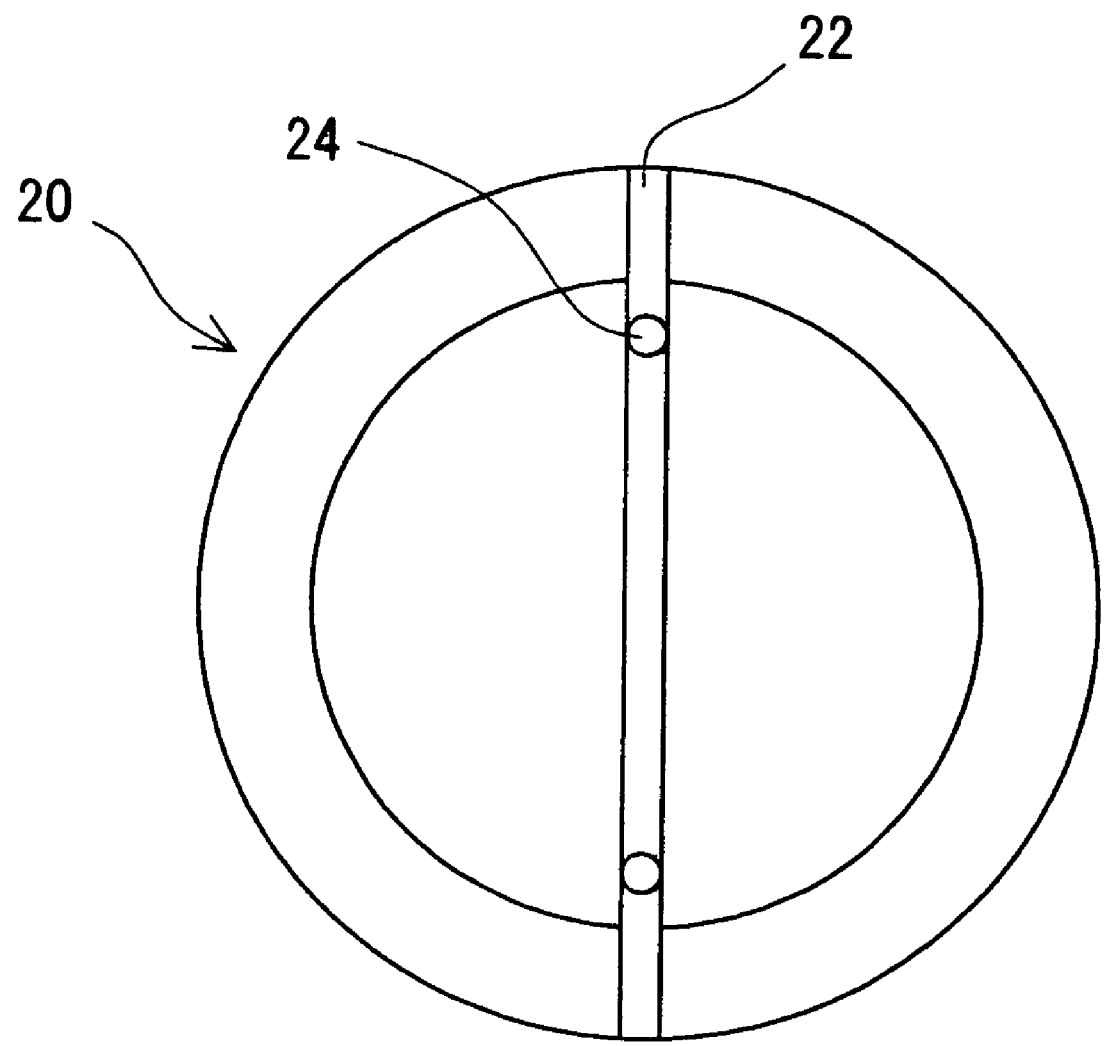
FIG. 4 is a bottom view of a bottom cover of the fluid container.

Meanwhile, as shown in the bottom view of FIG. 4, the bottom cover 20 includes at least one groove or depressed portion 22 that has at least one, preferably a plurality of through-holes 24 vertically extending though the bottom cover. Thus, the container body 10 includes a pressurizing space 26 defined by the side wall 14, the bottom cover 20, and the slidable valve 40, which is in communication with the ambient air.

As will be described in detail hereinafter, when the airless pump 3 is hermetically connected with the upper opening 11 of the fluid container 2 for sucking the fluid held within the container space 18 of the container body 10, because of no air introduced into the container body 10, the container space 18 receives a negative pressure. On the other hand, since the pressurizing space 26 is maintained at atmospheric pressure through the through-hole 24, the slidable valve 40 in the container space 18 is pushed upwardly by the atmospheric pressure in the pressurizing space 26. Therefore, the slidable valve 40 of the fluid container 2 moves upwardly from an unused position shown in FIG. 5A, gradually in response to the amount of the fluid sucked by the airless pump 3, and when the fluid is fully dispensed from the container space 18, the valve surface 42 closely contacts against the spacer surface 32 as shown in FIG. 5B.

According to the fluid container 2 of the present invention, as illustrated in the cross sectional view of FIG. 3, the spacer surface 32 of the annular spacer 30 and the valve surface 42 of the slidable valve 40 are inclined at tilt angles of $\theta_1$, $\theta_2$, respectively, relative to the horizontal surface. Even if the air bubble is trapped and attached on the spacer surface 32 of the annular spacer 30 when the fluid container 2 is filled in with the fluid at the manufacturer of the airless fluid dispensing system, the inclined surfaces facilitate the trapped air bubble on the spacer surface 32 to easily be evacuated from the upper opening 11 of the fluid container 2 along the inclined spacer surface 32. The tilt angles $\theta_1$ of the spacer surface 32 is set in a range between 5 and 30 degrees, and preferably between 15 and 25 degrees to securely evacuate the air bubble possibly trapped when filling the fluid container 2 with the fluid. Therefore, according to the present invention, the tilt angle $\theta_1$ of the spacer surface 32 is designed in the above given range so as to surely prevent the small air bubble from being entered and trapped in the container body 10, thereby eliminating the undesired pumping actions prior to use of the airless fluid dispensing system.

More preferably, the tilt angles of $\theta_1$, $\theta_2$ of the spacer surface 32 and the valve surface 42 are designed as being substantially equal ($\theta_1 = \theta_2$) to have complementary configurations, so as to closely contact to each other as shown in FIG. 5B, after completion of usage of the airless fluid dispensing system. This minimizes the amount of the useless fluid which remains in the container space 18 but cannot be dispensed even at the completion of usage.

It should be noted that the components of the fluid container 2 may be formed of any materials as is clear for a person skilled in the art. Although not limited thereto, preferably, the container body 10, the bottom cover 20, and the slidable valve 40 may be formed of resin material such as polypropylene and the annular spacer 30 may be made of low-density polyethylene. When formed of such materials, the annular spacer 30 can be fixed with the shoulder member 13 of the container body 10 in a close (well-sealed) manner.

Also, the tilt angles of $\theta_1$, $\theta_2$ of the spacer surface 32 and the valve surface 42 are not always equal, rather designed as being different from each other. For example, in case where the slidable valve 40 is made of elastic material such as elastomer, the tilt angle of $\theta_1$ of the spacer surface 32 may be set greater than the tilt angle of $\theta_2$ of the valve surface 42, so that the contacting region between the spacer surface 32 and valve surface 42 is expanding from the peripheral area to the central area as the slidable valve moves upwardly. This allows the fluid in the container space 18 to be squeezed towards the central area just before completion of the usage, thereby fully dispense the fluid in the container space 18 without remaining useless fluid therein.

Figure 6:
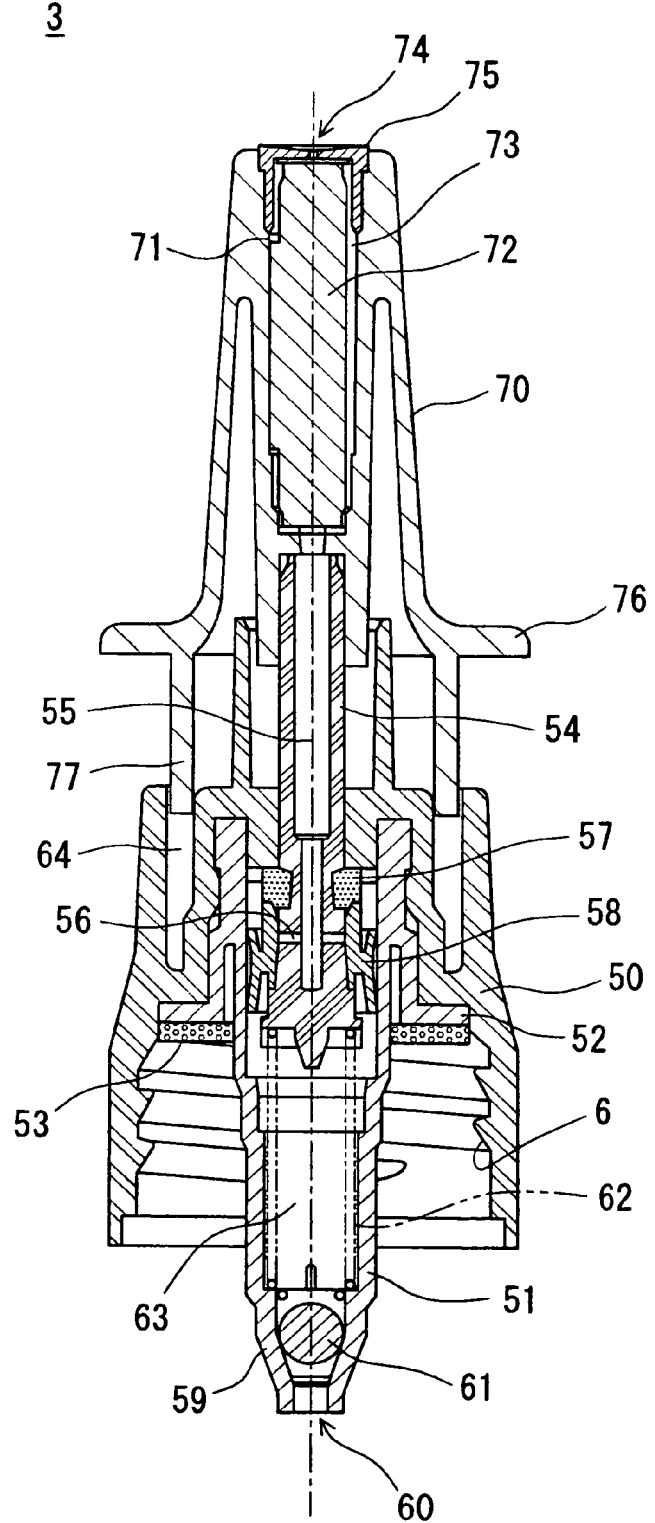
FIG. 6 is an enlarged cross sectional view of the airless pump of FIG. 2.
Figure 7:
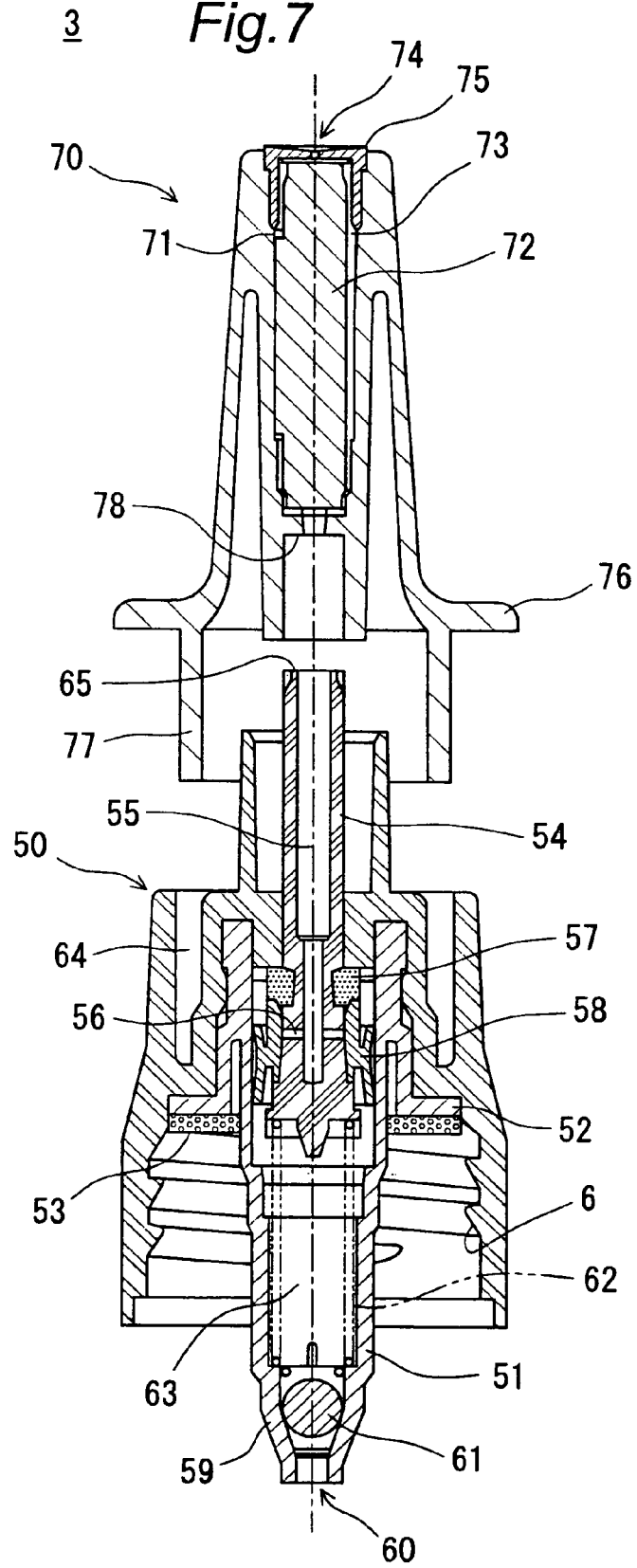
FIG. 7 is an exploded cross sectional view of the airless pump similar to FIG. 6, with a pump housing separated from a spout.

Next, referring to FIGS. 6 and 7, structure and operation of the airless pump 3 will be described herein. FIG. 6 is an enlarged cross sectional view of the airless pump 3, and FIG. 7 is an exploded cross sectional view thereof similar to FIG. 6, with a pump housing 50 separated from a spout 70.

Inside the pump housing 50, a vertically extending cylinder 51 is provided having a horizontally extending cylinder flange 52 with a gasket 53 thereon. The pump housing 50 has the internal thread 6, and as stated above, engagement of an external thread 5 of the fluid container 2 with the internal thread 6 causes hermetical sealing connection between the pump housing 50 and the fluid container 2.

Also provided within the pump housing 50 is a vertically movable piston 54. The piston 54 includes a vertical bore 55 extending along a central axis and a horizontal bore 56 extending through and in communication with the vertical bore 55. An annular stopper 57 made of elastic material such as rubber is provided around a small-diameter portion of the piston 54 which has reduced diameter in a horizontal direction. Also inside the cylinder 51, an annular sealing valve 58 that can be slidable along the inside surface of the cylinder 51 is provided to engage with the annular stopper 57. The cylinder 51 further includes a suction inlet 60 for sucking the fluid from the container body 10 through a bottom reduced-diameter portion 59. A ball valve 61 is arranged adjacent to the reduced-diameter portion 59, and a coil spring 62 shown by two-dot line in FIG. 7 is provided between the ball valve 61 and the piston 54. Thus, a suction chamber 63 for receiving the fluid is defined between the ball valve 61, the cylinder 51 (the inside surface thereof), and the piston 54, and the annular sealing valve 58.

Meanwhile, the spout 70 includes an inner wall 71 extending vertically, and a solid rod 72 spaced from and extending through the inner wall 71. Thus, a through-channel 73 is defined between the inner wall 71 of the spout 70 and the solid rod 72, vertically extending therethrough. Also, the spout 70 has a nozzle 75 performing as a spraying outlet 74 secured at the tip thereof. Further, the spout 70 includes an annular flange 76 extending horizontally and a tubular guiding wall 77 extending vertically therefrom.

In operation of the airless pump 3, when a user depresses the annular flange 76 of the spout 70, the tubular guiding wall 77 is guided into an annular slit 64 of the pump housing 50 and the lower end 78 of the spout 70 contacts with an upper end 65 of the piston 54, thereby pushing the piston 54 downwardly (see FIG. 7). With the piston 54 depressed, the annular stopper 57 is depressed, through which the annular sealing valve 58 also slides downwardly. This defines a small gap between the inner surface of the annular sealing valve 58 and the outer surface of the piston 54. Further depression of the piston 54 pressurizes the fluid received in the suction chamber 63, and a given amount of the fluid in response to the depression of the piston 54 is forced to run from the suction chamber 63 via the gap between the annular sealing valve 58 and the piston 54 through the horizontal and vertical bores 56, 55 and the through-channel 73 up to the nozzle 75, thereby being sprayed from the spraying outlet 74.

When the user releases the annular flange 76, the coil spring 62 in the cylinder 51 biases to move the piston 54 upwardly by its elasticity. This closes the gap between the inner surface of the annular sealing valve 58 and the outer surface of the piston 54, and also releases the ball valve 61 to form a gap between the ball valve 61 and the cylinder 51 (its inner surface), allowing the fluid to be sucked through this gap into the suction chamber 63. As mentioned above, as the piston 54 is raised, the gap between the annular sealing valve 58 and the piston 54 is closed, so that no air is introduced into the suction chamber 63 from the outside. Therefore, according to the present airless pump 3, no air bubble is introduced into the suction chamber 63 and the container space 18, thereby minimizing the variation of the dosage of the fluid.

When depressing the airless pump 3, the user typically pushes down the annular flange 76 of the spout 70 with his or her forefinger and middle finger while supporting the bottom cover 20 with his or her thumb. Since the through-holes 24 of the bottom cover 20 for communicating the pressurizing space 26 with the ambient air is provided within the groove or depressed portion 22, it is advantageously possible to avoid blockage of the through-holes 24 by user's thumb. Therefore, according to the fluid container 2 of the present invention, the pressurizing space 26 can always be kept at the atmospheric pressure so that the slidable valve 40 slides in good response to the amount of fluid in the container space 18, thereby securely preventing introduction of the air bubble into the suction chamber 63 of the airless pump 3.

Second Embodiment

Referring to FIGS. 8-11, a second embodiment of the airless fluid dispensing system according to the present invention will be described herein. Since the airless fluid dispensing system of the second embodiment is similar to that of the first embodiment except the structure of the fluid container 2, duplicate description will be eliminated.

Figure 8:
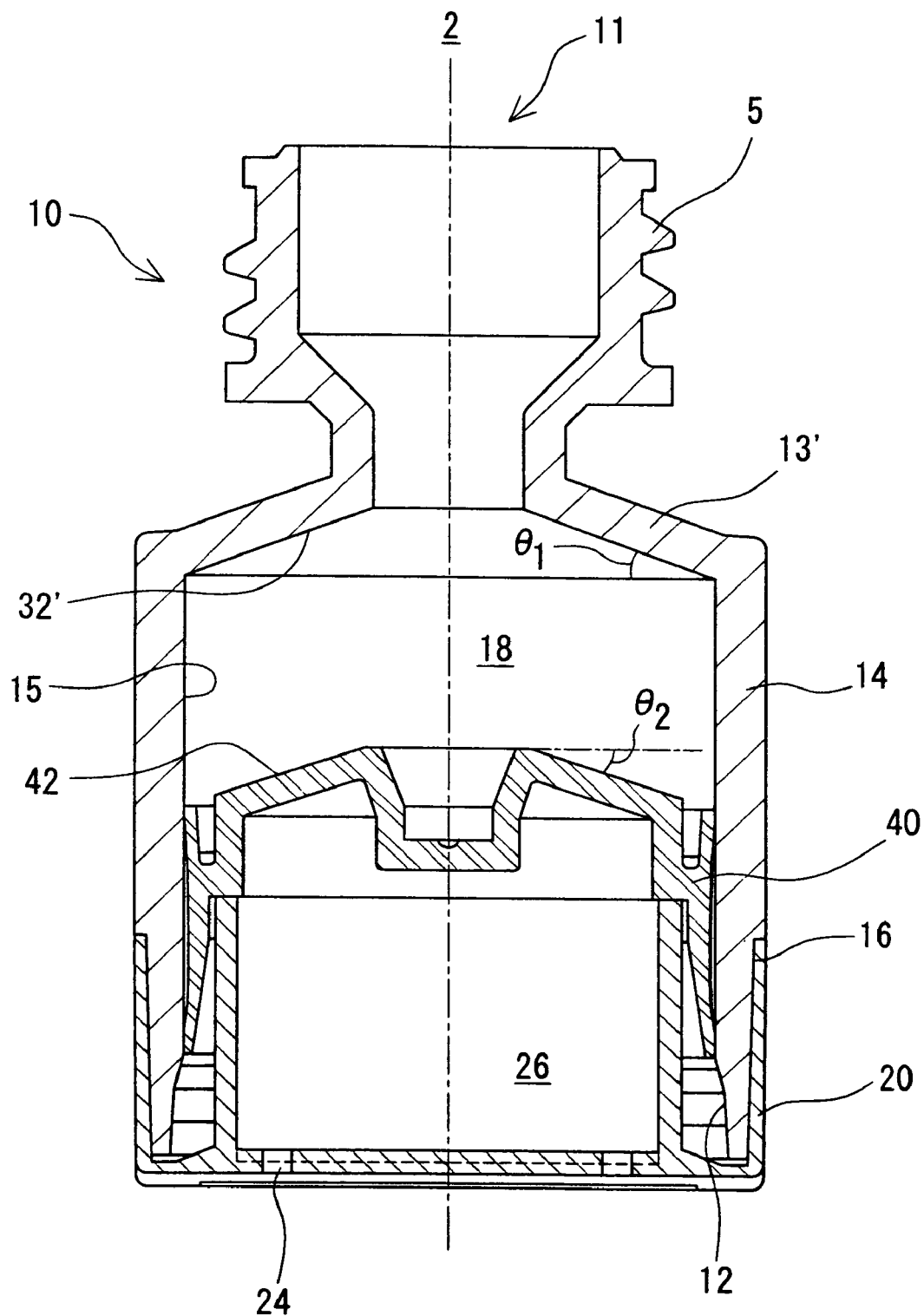
FIG. 8 is an enlarged cross sectional view of the fluid container according to the second embodiment of the present invention.
Figure 9:
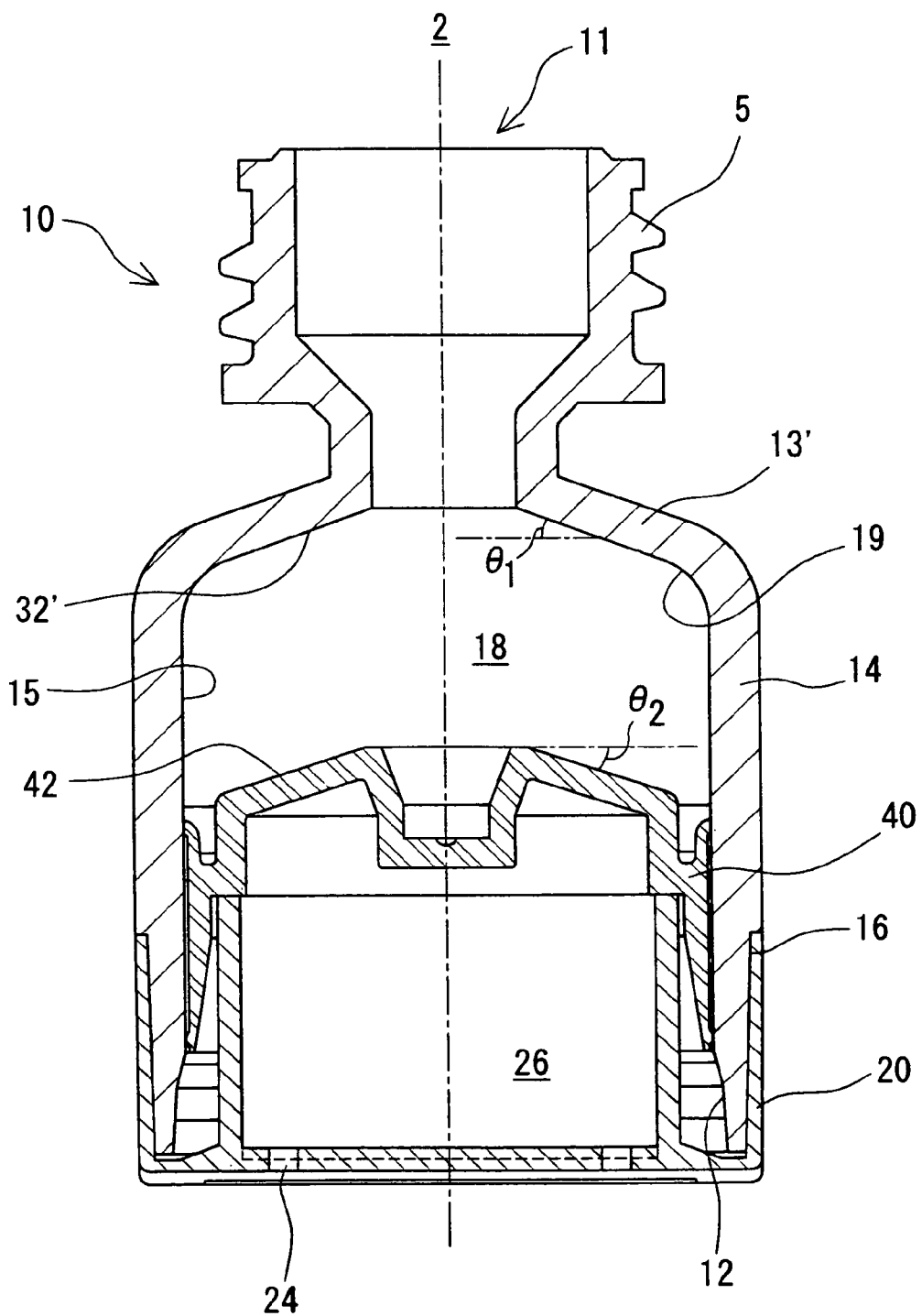
FIG. 9 is an enlarged cross sectional view of the fluid container of Modification 1.

In the fluid container 2 of the first embodiment, the shoulder member 13 of the container body 10 and the annular spacer 30 are designed as separate components. On the other hand, in the fluid container 2 of the second embodiment, as illustrated in FIG. 8, the annular spacer is integrally formed with the shoulder member of the container body 10 and a shoulder surface 32' of the shoulder 13' opposing to the valve surface of the slidable valve 40 is inclined at the tilt angle of $\theta_1$ relative to the horizontal surface. Therefore, according to the fluid container 2 of the second embodiment, the manufacturing cost can be reduced by decreasing the number of the components while achieving the same advantages as the first embodiment.

[Modification 1]

The fluid container 2 of the second embodiment can be modified so that the shoulder surface 32' is formed to be substantially continuous with the inner surface 15 of the side wall 14 via a curved surface 19. This arrangement surely prevents the small air bubble from being trapped at a discontinuous region between the shoulder surface 32' and the side wall 14 while filled in with the fluid. Similarly, the fluid container 2 of the first embodiment can be modified so that the continuous curved surface is provided between the inner surface 15 of the side wall 14 and the spacer surface 32 of the spacer 30, eliminating any stepped or discontinuous surface therebetween, for evacuation of the trapped air bubble.

[Modification 2]

The airless fluid dispensing system of the first and second embodiments are described above as spraying the fluid upwardly from the nozzle 75 provided at the tip of the spout 70, which is not limited thereto. The spraying outlet 74 of the nozzle 75 may be directed horizontally as shown in FIGS. 10 and 11, and operable to spray the fluid in the horizontal direction also by depressing the spout 70. This further expands the scope of applications of the airless fluid dispensing system according to the present invention.

[Experiment 1]

With following experiments, the advantages of the present inventions will be described herein in detail. While any fluid can be applied to the present invention, for example, three kinds of gel type mucoadhesive agents were prepared, which have viscosity different from one another such as ones used for a nasal drop, as listed below. The viscosity thereof was measured by means of a viscometer C type at 20 degrees centigrade. It should be noted that those fluid contain no pharmaceutically active substantive.

TABLE 1

| | Ingredients of Fluid 1, 2, 3 | | |
|---|---|---|---|
| Ingredient | Fluid 1 (1000 mPa · s) | Fluid 2 (2000 mPa · s) | Fluid 3 (3600 mPa · s) |
| carboxy vinyl polymer | 0.42 | 0.53 | 0.56 |
| L-arginine | 0.74 | 0.95 | 1.00 |
| edetate sodium | 0.05 | 0.05 | 0.05 |
| polysorbate 80 | 0.10 | 0.10 | 0.10 |
| concentrated glycerin | 1.00 | 1.00 | 1.00 |
| sodium chloride | 0.50 | 0.50 | 0.50 |
| purified water | 97.19 | 96.87 | 96.79 |
| Total | 100% | 100% | 100% |

Also, three of airless fluid dispensing systems which can spray 100 mg of the fluid with a single pumping action were prepared, i.e., according to the present invention (referred to simply as "Invention"), and according to the conventional technique (referred to simply as "Comparison 1" and "Comparison 2"). Those airless fluid dispensing systems were filled with five (5) grams of each of Fluid 1, 2, 3, individually for following experiments.

Invention, Comparison 1 and Comparison 2 were filled with Fluid 1 (viscosity: 1000 mPa·s), and the fluid weight (mg) sprayed by each pumping action was plotted in accordance with the number of pumping actions, thereby to obtain the chart of FIG. 12. As clearly illustrated in this chart, the dispensing system of Invention was able to continuously supply the predetermined or expected dosage (referred to as "preset dosage D", which was set as 100 mg in the experiments) just before all of the fluid was dispensed. On the contrary, the dispensing systems of Comparison 1 and Comparison 2 dispensed the fluid less than the preset dosage, thus, were not able to spray the preset dosage of the fluid after thirty (30) through forty (40) pumping actions.

Figure 13:
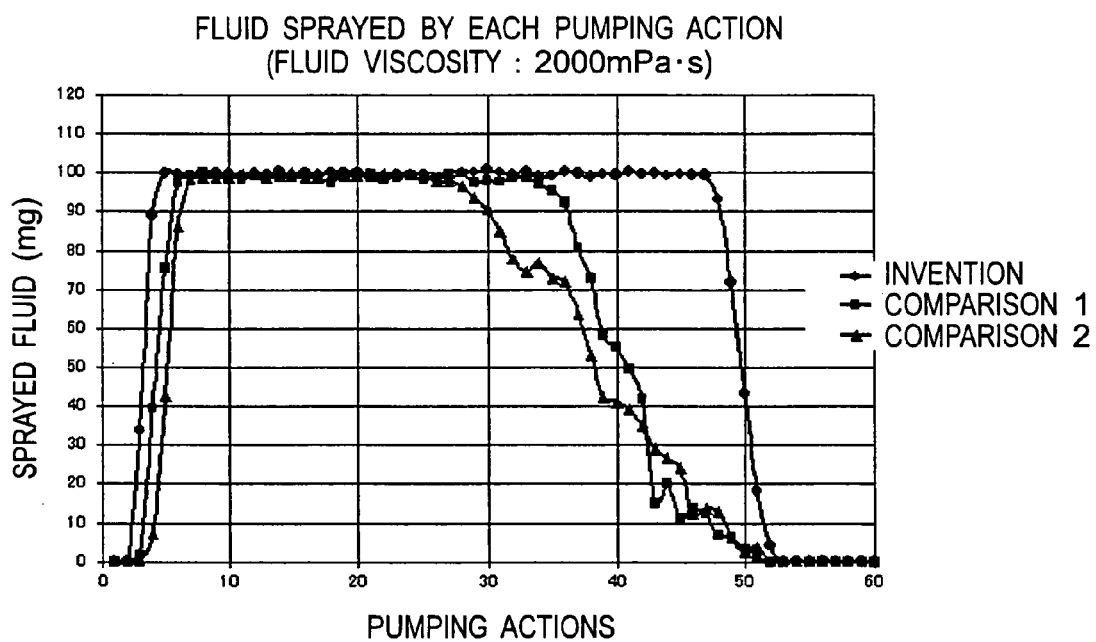
FIG. 13 is a chart showing relationship between fluid weight (viscosity: 2000 mPa·s) sprayed by each pumping action and the number of pumping actions.
Figure 14:
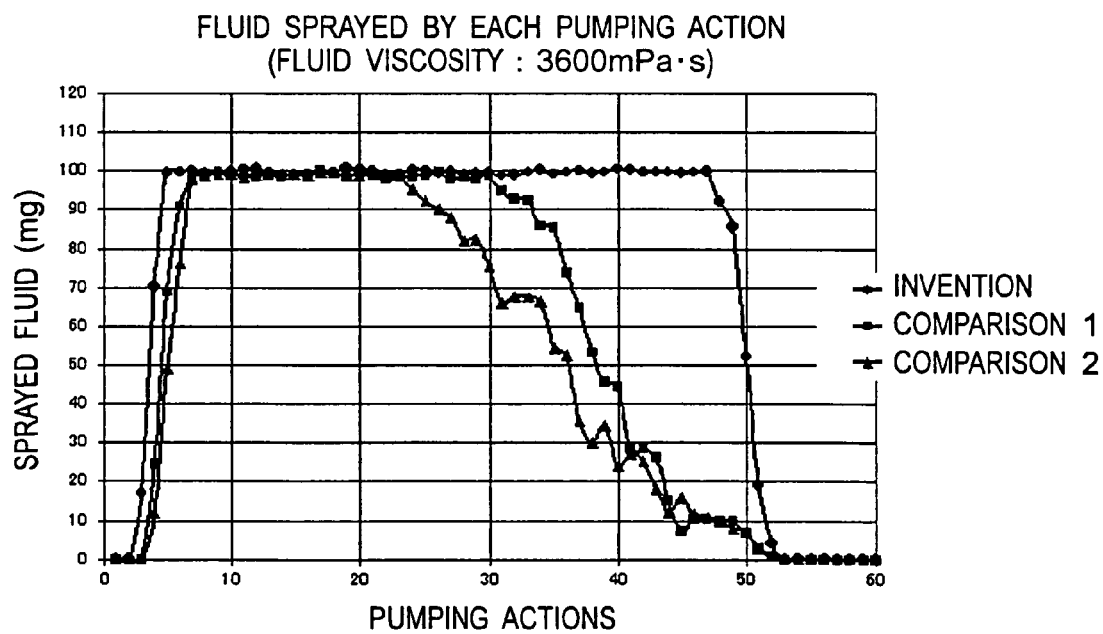
FIG. 14 is a chart showing relationship between fluid weight (viscosity: 3600 mPa·s) sprayed by each pumping action and the number of pumping actions.
Figure 15A:
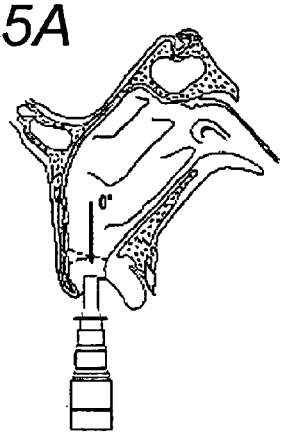
FIGS. 15A-15G illustrate the airless fluid dispensing system used for spraying the fluid into the nose at various spraying angles.
Figure 15B:
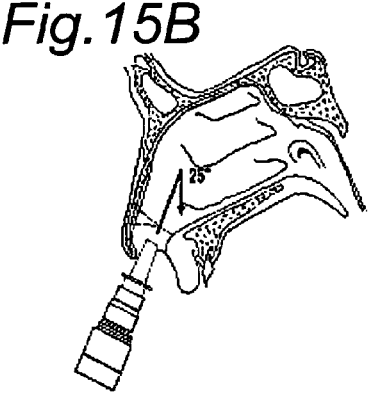
Figure 15C:
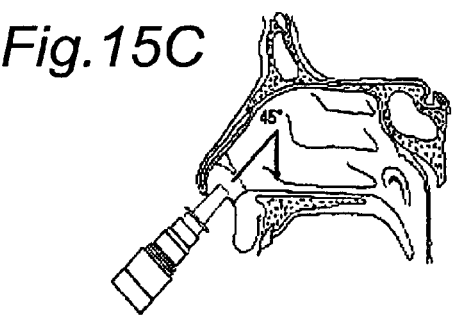
Figure 15D:
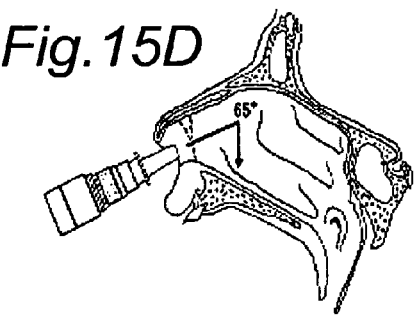
Figure 15E:
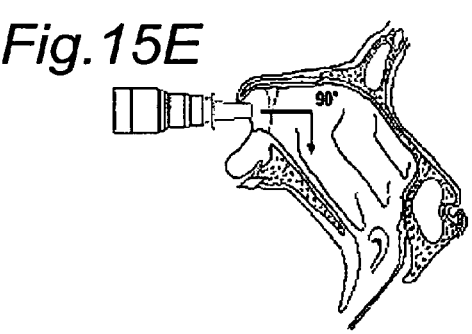
Figure 15F:
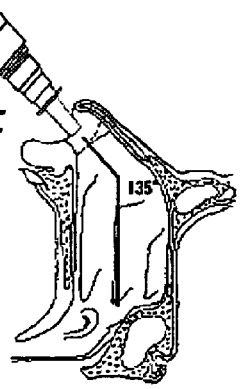
Figure 15G:
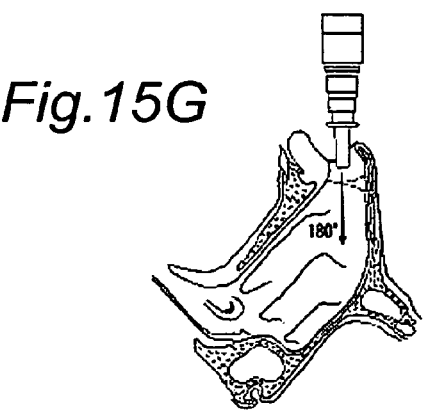

Similarly, the dispensing systems of Invention, Comparison 1 and Comparison 2 were filled also with Fluid 2 (viscosity: 2000 mPa·s) and Fluid 3 (viscosity: 3600 mPa·s), and the fluid weight (mg) sprayed by each pumping action were plotted in accordance with the number of pumping actions, thereby to obtain the charts of FIGS. 13 and 14, respectively. As clearly shown in these charts, despite variation of viscosity of the fluid, the dispensing system of Invention was able to continuously spray the preset dosage just before all of the fluid was dispensed, however, the dispensing systems of Comparison 1 and 2 were not able to spray the preset dosage of the fluid even though sufficient amount of the fluid remains in the fluid container. Therefore, the dispensing system of Invention is much more advantageous than those of Comparison 1 and Comparison 2 in dispensing the sprayed fluid in an expected and stable manner.

Next, another comparison experiments were made for the dispensing systems of Invention, Comparison 1 and Comparison 2, regarding how much amount of the fluid can be completely used and how stably the fluid can be dispensed. Firstly, some particular values are defined as follows:

$W_O$: Weight of fluid initially filled in each dispensing system (which is 5 grams in this experiment);
$W_E$: Weight of fluid remained in each dispensing system at completion of usage (unit: gram);
$D_{IN}$: Single dosage when it falls within a range of the preset dosage plus/minus 10% (which is between 90-110 mg in this experiment);
$D_{OUT}$: Single dosage when it fails to fall within a range of the preset dosage plus/minus 10% (which is less than 90 mg or greater than 110 mg in this experiment);
$\Sigma D_{IN}$: Total dosages of $D_{IN}$ dispensed by all pumping actions; and
$\Sigma D_{OUT}$: Total dosages of $D_{OUT}$ dispensed by all pumping actions.

When defined as above, Remaining Ratio of Fluid, Dispensing Ratio Within Preset Dosage, and Dispensing Ratio Beyond Preset Dosage can be defined as follows:

Remaining Ratio of Fluid (%)=$W_E/W_O \times 100$;

Dispensing Ratio Within Preset Dosage (%)=$\Sigma D_{IN}/W_O \times 100$;

and

Dispensing Ratio Beyond Preset Dosage (%)=$\Sigma D_{OUT}/W_O \times 100$.

Therefore, the number of dosages which falls within the preset dosage plus/minus 10% (which is between 90-110 mg in this experiment) by single pumping action is referred as to "Dispensing Number Within Preset Dosage".

According to the above definition, as Remaining Ratio of Fluid is lower, more amount of the fluid can effectively be dispensed without wasting. Also, it is preferable that the preset dosages can be dispensed in a stable manner with greater Dispensing Ratio Within Preset Dosage, lower Dispensing Ratio Beyond Preset Dosage, and greater Dispensing Number Within Preset Dosage. With data for plotting the charts of FIGS. 12-14, Remaining Ratio of Fluid, Dispensing Ratio Within Preset Dosage, Dispensing Ratio Beyond Preset Dosage, and Dispensing Number Within Preset Dosage were calculated as listed below.

TABLE 2

Comparison of Remaining Ratio of Fluid and others for variable fluid viscosity

|  | Fluid (visicosity) | Remaining Ratio of Fluid (%) | Dispensing Ratio Within Preset Dosage (%) | Dispensing Ratio Beyond Preset Dosage (%) | Dispensing Number Within Preset Dosage |
|---|---|---|---|---|---|
| Invention | Fluid 1 (1000 mPa·s) | 7.1 | 87.8 | 5.1 | 44 |
|  | Fluid 2 (2000 mPa·s) | 7.2 | 87.6 | 5.2 | 44 |
|  | Fluid 3 (3600 mPa·s) | 7.3 | 87.7 | 5.0 | 44 |
| Comparison 1 | Fluid 1 (1000 mPa·s) | 24.4 | 65.4 | 10.2 | 33 |
|  | Fluid 2 (2000 mPa·s) | 27.7 | 61.0 | 11.3 | 31 |
|  | Fluid 3 (3600 mPa·s) | 31.3 | 54.7 | 14.0 | 28 |
| Comparison 2 | Fluid 1 (1000 mPa·s) | 28.5 | 55.1 | 16.4 | 28 |
|  | Fluid 2 (2000 mPa·s) | 32.8 | 47.2 | 20.0 | 24 |
|  | Fluid 3 (3600 mPa·s) | 38.6 | 39.2 | 22.2 | 20 |

As clearly indicated in Table 2, Remaining Ratio of Fluid of Invention is substantially lower than those of Comparison 1 and Comparison 2, thus, the dispensing system of Invention can effectively dispense almost all of the fluid. Also, Remaining Ratio of Fluid of Invention is independent upon viscosity of the fluid relative to those of Comparison 1 and Comparison 2. Therefore, the dispensing system of Invention can be applicable for dispensing any fluids having a wide variety of viscosity. Also, according to the dispensing system of Invention, Dispensing Ratio Within Preset Dosage is excellent (more than 87%, irrelevant to viscosity of the fluid), Dispensing Ratio Beyond Preset Dosage is low, and Dispensing Number Within Preset Dosage is remarkable, relative to those of Comparison 1 and Comparison 2. Therefore, the dispensing system of Invention can dispense the expected preset dosage of the fluid in a quite stable manner.

Figure 16:
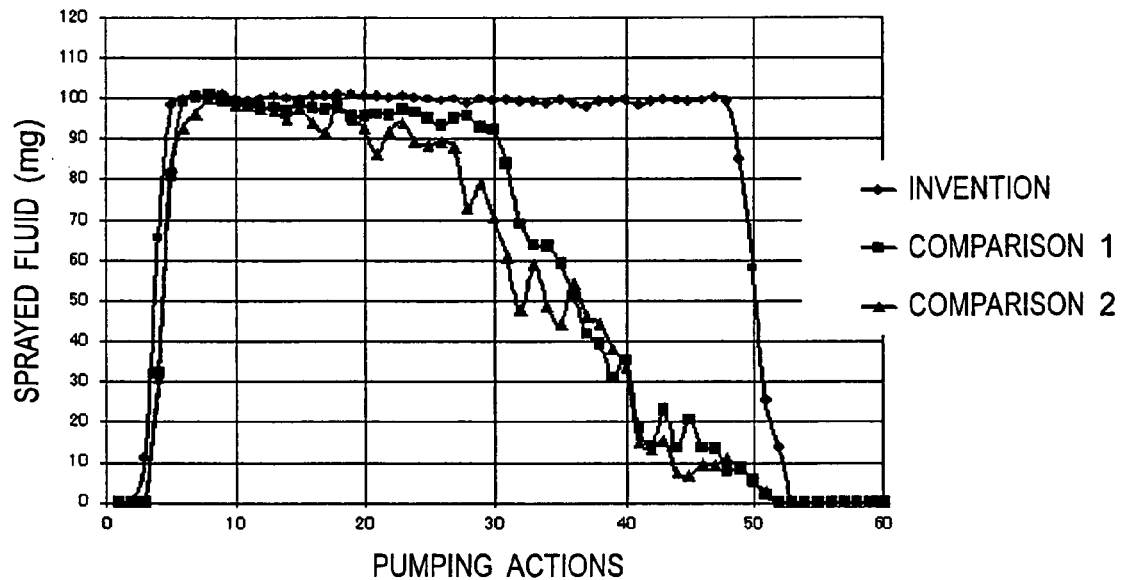
FIG. 16 is a chart showing relationship between fluid weight sprayed by each pumping action at the spraying angle of 45 degrees and the number of pumping actions.
Figure 17:
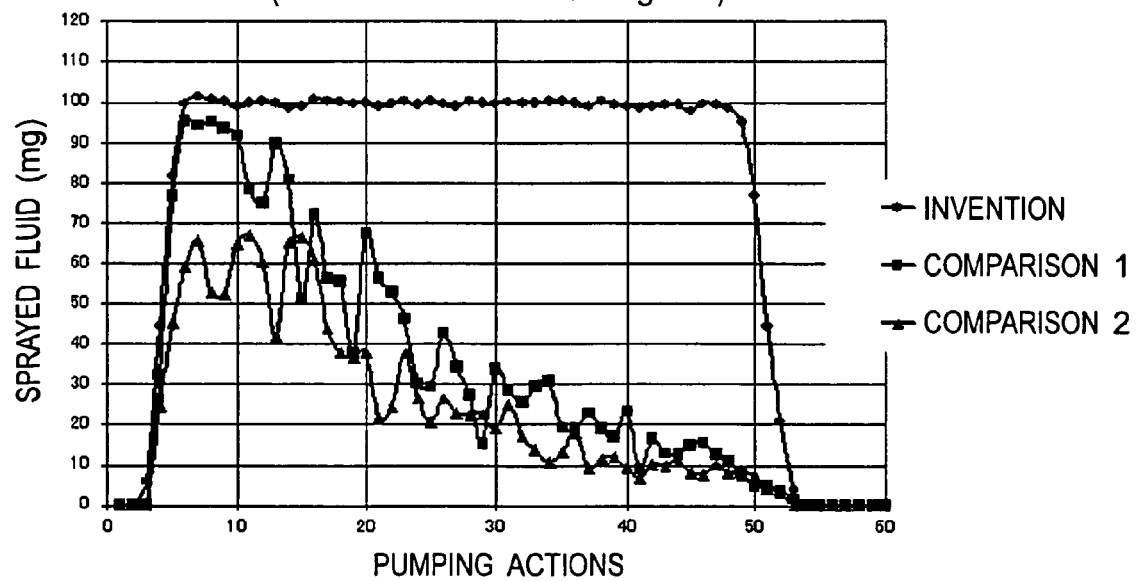
FIG. 17 is a chart showing relationship between fluid weight sprayed by each pumping action at the spraying angle of 65 degrees and the number of pumping actions.
Figure 18:
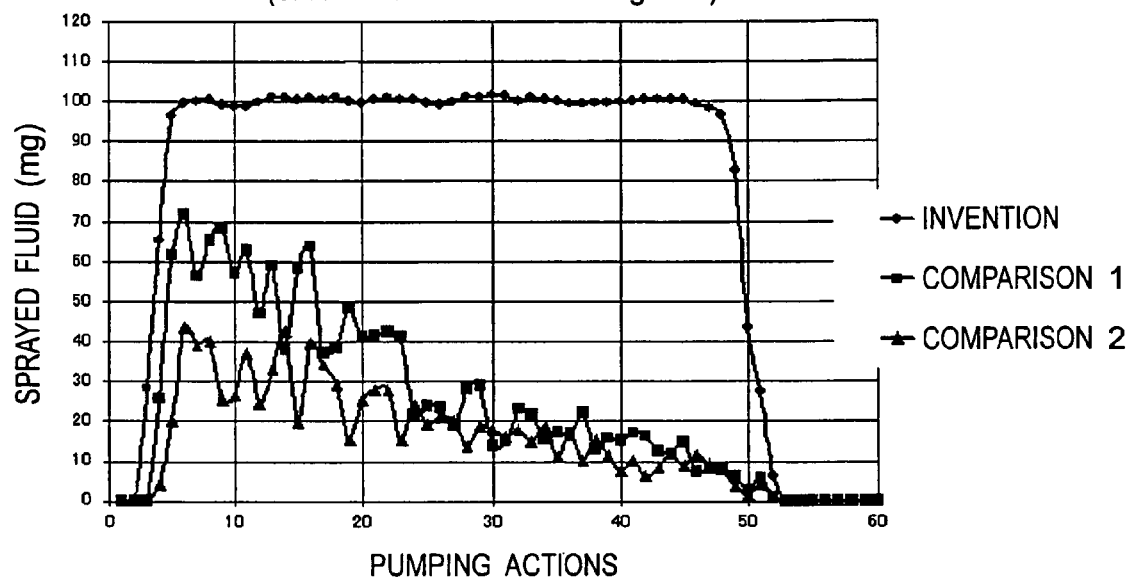
FIG. 18 is a chart showing relationship between fluid weight sprayed by each pumping action at the spraying angle of 90 degrees and the number of pumping actions.

Next, further comparison experiments were made for the dispensing systems of Invention, Comparison 1 and Comparison 2, regarding how much amount of the fluid can be completely used and how stably the fluid can be dispensed, when the fluid is sprayed into the nose at various spraying angles as illustrated in FIG. 15. In particular, after Fluid 2 (viscosity: 2000 mPa·s) is filled in the dispensing systems of Invention, Comparison 1 and Comparison 2, fluid weight (mg) sprayed by each pumping action at the spraying angle of 45 degrees shown in FIG. 15 was plotted in accordance with the number of pumping actions, thereby to obtain the chart of FIG. 16. As clearly illustrated in this graph, the dispensing system of Invention was able to continuously dispense the preset dosage just before all of the fluid was dispensed. On the contrary, the dispensing systems of Comparison 1 and 2 dispensed the fluid less than the preset dosage after twenty (20) through thirty (30) pumping actions, thus, were not able to spray the preset dosage of the fluid over the total pumping actions. Similarly, fluid weight (mg) sprayed at the spraying angle of 65 degrees and 90 degrees were plotted in accordance with the number of pumping actions, thereby to obtain the charts of FIGS. 17 and 18, respectively. As clearly illustrated in those graphs, despite variation of the spraying angles of the fluid, the dispensing system of Invention was able to continuously supply the preset dosage just before all of the fluid was dispensed, however, the dispensing systems of Comparison 1 and 2 were not able to spray the preset dosage of the fluid even though sufficient amount of the fluid remains in the fluid container. With the above results, the dispensing system of Invention has much more remarkable features over those of Comparison 1 and Comparison 2 for dispensing the sprayed fluid in an expected and stable manner.

Also, when the dispensing systems of Invention, Comparison 1 and Comparison 2, were used for spraying Fluid 2 into the nose at 0, 45, 65, 90 degrees, some measurements by each pumping action were made for Remaining Ratio of Fluid, Dispensing Ratio Within Preset Dosage, Dispensing Ratio Beyond Preset Dosage, and Dispensing Number Within Preset Dosage, as listed below.

TABLE 3

Comparison of Remaining Ratio of Fluid and others for variable spraying angles

|  | Spraying Angles | Remaining Ratio of Fluid (%) | Dispensing Ratio Within Preset Dosage (%) | Dispensing Ratio Beyond Preset Dosage (%) | Dispensing Number Within Preset Dosage |
|---|---|---|---|---|---|
| Invention | 0° | 7.2 | 87.6 | 5.2 | 44 |
|  | 45° | 7.1 | 87.7 | 5.2 | 44 |
|  | 65° | 7.1 | 87.4 | 5.5 | 44 |
|  | 90° | 7.1 | 87.8 | 5.1 | 44 |
|  | 180° | 7.1 | 87.7 | 5.2 | 44 |
| Comparison 1 | 0° | 27.7 | 61.0 | 11.3 | 31 |
|  | 45° | 35.7 | 48.5 | 15.8 | 25 |
|  | 65° | 60.7 | 9.4 | 29.9 | 5 |
|  | 90° | 70.7 | 0.0 | 29.3 | 0 |
| Comparison 2 | 0° | 32.8 | 47.2 | 20.0 | 24 |
|  | 45° | 40.3 | 34.3 | 25.4 | 18 |
|  | 65° | 72.8 | 0.0 | 27.2 | 0 |
|  | 90° | 81.4 | 0.0 | 18.6 | 0 |

As clear in Table 3, according to the dispensing system of Invention, irrelevant to the spraying angles, Remaining Ratio of Fluid is quite low, Dispensing Ratio Within Preset Dosage is great (more than 87%, regardless of the spraying angles), Dispensing Ratio Beyond Preset Dosage is low, and Dispensing Number Within Preset Dosage is remarkable. Therefore, the dispensing system of Invention can dispense the expected preset dosage of the fluid without wasting the fluid in a quite stable manner, even if the spraying angles are varied.

In the foregoing, several embodiment and examples of the fluid container and the airless fluid dispensing system using thereof according to the present invention are described, the airless fluid dispensing system can be used for various applications for dispensing or applying to an application site, fluids containing medical products such as a nasal formulation, eye drops and disinfectants, and viscous fluids containing quasi-medical products such as a perfume, hair growth tonic and air freshener. It should be noted that the present invention is not to be interpreted as being limitative to those particular embodiments and examples, rather is defined by attached claims, therefore, modifications and/or changes as clear for those skilled in the art without departing from the sprit and scope of the present invention are to be included within a range of the present invention.

I claim:

1. A fluid container, comprising:
   a container body having upper and lower openings, and further having a shoulder member and a side wall which extend between the upper and lower openings;
   a spacer abutting on the shoulder member of said container body;
   a slidable valve slidably moving along an inner surface of the side wall of said container body in a hermetically sealed manner, said slidable valve defining a container space for holding fluid, in conjunction with the side wall of said container body; and
   a bottom cover covering across the lower opening of said container body;
   wherein said spacer and said slidable valve include a spacer surface and a valve surface, respectively, which oppose to each other and are inclined at tilt angles between 5 and 30 degrees relative to a horizontal surface, and
   wherein the tilt angle of the spacer surface relative to the horizontal surface is set greater than the tilt angle of the valve surface relative to the horizontal surface.

2. The fluid container according to claim 1, wherein the spacer surface and the valve surface have configurations complementary to each other.

3. The fluid container according to claim 1, wherein said spacer is integrally formed with the side wall of said container body.

4. The fluid container according to claim 1, wherein the spacer surface is formed to be substantially continuous with the inner surface of the side wall via a curved surface.

5. The fluid container according to claim 1, wherein said spacer is made of low-density polyethylene.

6. The fluid container according to claim 1, wherein said spacer is made of elastic material.

7. The fluid container according to claim 1, wherein said bottom cover includes a groove extending along a bottom surface thereof, said bottom cover having a through-hole through which a pressurizing space hermetically sealed by the side wall of said container body, the slidable valve, and the bottom cover is in communication with the ambient air.

8. An airless fluid dispensing system, comprising the fluid container according to claim 1, and an airless pump hermetically connected to the upper opening of the fluid container.

9. A fluid container, comprising:
   a container body having upper and lower openings, and further having a shoulder member and a side wall which extend between the upper and lower openings;
   a slidable valve slidably moving along an inner surface of the side wall of said container body in a hermetically sealed manner, said slidable valve defining a container space for holding fluid, in conjunction with the side wall of said container body; and
   a bottom cover covering across the lower opening of said container body;
   wherein said shoulder member and said slidable valve include a shoulder surface and a valve surface, respectively, which oppose to each other and are inclined at tilt angles between 5 and 30 degrees relative to a horizontal surface, and
   wherein the tilt angle of the shoulder surface relative to the horizontal surface is set greater than the tilt angle of the valve surface relative to the horizontal surface.

10. The fluid container according to claim 9, wherein the shoulder surface and the valve surface have configurations complementary to each other.

11. The fluid container according to claim 9, wherein the shoulder surface is formed to be substantially continuous with the inner surface of the side wall via a curved surface.

12. The fluid container according to claim 9, wherein said bottom cover includes a groove extending along a bottom surface thereof, said bottom cover having a through-hole through which a pressurizing space hermetically sealed by the side wall of said container body, the slidable valve, and the bottom cover is in communication with the ambient air.

13. An airless fluid dispensing system, comprising the fluid container according to claim 9, and an airless pump hermetically connected to the upper opening of the fluid container.

* * * * *